United States Patent
Huang et al.

(10) Patent No.: US 11,959,881 B2
(45) Date of Patent: Apr. 16, 2024

(54) NON-DESTRUCTIVE TESTING METHOD FOR FLEXURAL STRENGTH OF FINE CERAMIC, APPARATUS, AND STORAGE MEDIUM

(71) Applicants: DONGGUAN CITY WONDERFUL CERAMICS INDUSTRIAL PARK CO., LTD., Guangdong (CN); JIANGXI HEMEI CERAMICS CO., LTD., Jiangxi (CN); GUANGDONG JIAMEI CERAMICS CO., LTD, Guangdong (CN)

(72) Inventors: Jianping Huang, Dongguan (CN); Yuezeng Xie, Dongguan (CN); Kehui Lin, Dongguan (CN); Hailong Yu, Dongguan (CN)

(73) Assignees: DONGGUAN CITY WONDERFUL CERAMICS INDUSTRIAL PARK CO., LTD., Dongguan (CN); JIANGXI HEMEI CERAMICS CO., LTD., Yichun (CN); GUANGDONG JIAMEI CERAMICS CO., LTD, Qingyuan (CN)

( * ) Notice: Subject to any disclaimer, the term of this patent is extended or adjusted under 35 U.S.C. 154(b) by 417 days.

(21) Appl. No.: 17/421,598

(22) PCT Filed: Mar. 18, 2020

(86) PCT No.: PCT/CN2020/079888
§ 371 (c)(1),
(2) Date: Jul. 8, 2021

(87) PCT Pub. No.: WO2021/184236
PCT Pub. Date: Sep. 23, 2021

(65) Prior Publication Data
US 2022/0341878 A1     Oct. 27, 2022

(51) Int. Cl.
*G01N 29/04*     (2006.01)
*G01N 33/38*     (2006.01)
*G01N 35/00*     (2006.01)

(52) U.S. Cl.
CPC ........... *G01N 29/04* (2013.01); *G01N 33/388* (2013.01); *G01N 35/00584* (2013.01); *G01N 2291/0232* (2013.01)

(58) Field of Classification Search
CPC .................. G01N 3/52; G01N 33/388; G01N 2291/0232; G01N 2203/0023
See application file for complete search history.

(56) References Cited

U.S. PATENT DOCUMENTS

2016/0282230 A1 *  9/2016  Poser .................... G01M 99/00
2019/0178765 A1    6/2019  Saleem

FOREIGN PATENT DOCUMENTS

CN      1712961 A      12/2005
CN    104251882 A      12/2014
(Continued)

OTHER PUBLICATIONS

Screening Eagle; SONREB method and how easily it can be realized using Proceq instruments; https://www.facebook.com/Screening Eagle/videos/sonreb-method-and-how-easily-it-can-be-realized-using-proceq-instruments/483171592505313/; accessed on Oct. 25, 2023; published Jul. 3, 2019. (Year: 2019).*

(Continued)

*Primary Examiner* — Daniel J Colilla
(74) *Attorney, Agent, or Firm* — Maier & Maier, PLLC (57) ABSTRACT

A non-destructive testing method for flexural strength of fine ceramic, an apparatus, and a storage medium, including adjusting an uncut intact fine ceramic test sample to an ultrasonic testing position, and fixing the test sample; adjusting an ultrasonic testing instrument, controlling and adjust-
(Continued)

ing the positions of ultrasonic testing probes of the ultrasonic testing instrument until the ultrasonic testing probes, the fine ceramic test sample and the resiling direction are located on the same plane, performing ultrasonic testing on the test sample, and collecting ultrasonic testing data of the test sample; adjusting the position of the fine ceramic test sample until a resilience testing rod and the test sample are located on the same plane and fixed, performing resilience testing on the test sample, and collecting resilience testing data of the test sample; and building a data model, or substituting testing data into the pre-built data model.

10 Claims, 2 Drawing Sheets

(56) References Cited

FOREIGN PATENT DOCUMENTS

| CN | 105352831 A | 2/2016 |
|----|-------------|--------|
| CN | 105842076 A | 8/2016 |
| CN | 109142050 A | 1/2019 |
| CN | 109781847 A | 5/2019 |
| CN | 110672822 A | 1/2020 |
| JP | S6326546 A | 2/1988 |
| JP | 2007333498 A | 12/2007 |
| JP | 2013054020 A | 3/2013 |
| JP | 2019007869 A | 1/2019 |

OTHER PUBLICATIONS

FPRimeC.com; What is the SonReb method? | Non-Destructive Testing; https://www.youtube.com/watch?v=ksheRM9Xth4; accessed on Oct. 25, 2023; published Aug. 16, 2019. (Year: 2019).*
Harrison et al.; Impact resistance of ceramic tiles and flooring; 1992; International Ceramics Journal (Testo Stampato); 14(55), 31-35. (Year: 1992).*
Boccaccini et al., Quality Control and Thermal Shock Damage Characterization of High-Temperature Ceramics by Ultrasonic Pulse Velocity Testing; 2007; International Journal of Applied Ceramic Technology; 4[3], pp. 260-268. (Year: 2007).*
Machine translation of Du et al. (CN 105842076 A); Aug. 10, 2016. (Year: 2016).*
Translation of International Search Report dated Dec. 23, 2020 in corresponding International Application No. PCT/CN2020/079888; 3 pages.

* cited by examiner

NON-DESTRUCTIVE TESTING METHOD FOR FLEXURAL STRENGTH OF FINE CERAMIC, APPARATUS, AND STORAGE MEDIUM

TECHNICAL FIELD

The present disclosure relates to the technical field of testing of flexural strength of fine ceramic, and particularly relates to a non-destructive testing method for flexural strength of fine ceramic, an apparatus, and a storage medium.

BACKGROUND

At present, the testing of the flexural strength of fine ceramic products mainly refers to the standard GB/T6569-2006 "Fine Ceramics (advanced Ceramics, advanced Technical Ceramics)—Test Method for Flexural Strength of Monolithic Ceramics At Room Temperature", and most of existing testing devices for the flexural strength of a fine ceramic material are not suitable for large-size test samples (such as a platy product having an upper surface area larger than or equal to 1.62 $m^2$, a hollow product, an arc-shaped product, or a product of a specially-shaped structure). This causes that existing testing of the flexural strength of the fine ceramic is carried out using destructive testing measures or methods. That is to say, the testing can be carried out only by machining a test sample to an appropriate size. That is, the fine ceramic material itself needs to be cut and tailored, and then a small-size material obtained by cutting is tested, which causes that the large-size product is destroyed and that the sample to be tested cannot be reused after the destructive testing, resulting in great waste. In addition, such destructive testing will destroy the performance of the material. Compared with the performance of the material, test results may have large testing errors, which cannot truly characterize the flexural strength of the material.

Therefore, the prior art has defects and needs to be improved and developed.

SUMMARY

The technical problem to be solved by the present disclosure is to provide a non-destructive testing method for flexural strength of fine ceramic, an apparatus, and a storage medium for the above-mentioned defects in the prior art. The present disclosure is directed to solve the problems in the prior art that large-size fine ceramic would be destroyed during testing of the flexural strength and cannot be reused, and tested data also has a larger error.

The technical solution used by the present disclosure to solve the technical problems is as follows: a non-destructive testing method for flexural strength of fine ceramic, including:

adjusting an uncut intact fine ceramic test sample to an ultrasonic testing position, and fixing the test sample;
adjusting an ultrasonic testing instrument, controlling and adjusting the positions of ultrasonic testing probes of the ultrasonic testing instrument till the ultrasonic testing probes, the fine ceramic test sample and a resiling direction are located on the same plane, performing ultrasonic testing on the test sample, and collecting ultrasonic testing data of the test sample;
adjusting the position of the fine ceramic test sample till a resilience testing rod and the test sample are located on the same plane and fixed, performing resilience testing on the test sample, and collecting resilience testing data of the test sample;
building a data model according to the ultrasonic testing data and the resilience testing data, or substituting the ultrasonic testing data and the resilience testing data into the pre-built data model to obtain flexural strength characterization data of the test sample.

Further, before adjusting the uncut intact fine ceramic test sample to the ultrasonic testing position, and fixing the test sample, the method further includes:

pre-constructing an ultrasonic and resilience two-parameter-based non-destructive testing system for flexural strength of fine ceramic;
the non-destructive testing system for flexural strength of fine ceramic includes an automatic control and testing mechanism and a data processing mechanism. The automatic testing mechanism also includes a sample installation component, an ultrasonic testing component and a resilience testing component.

Further, before performing non-destructive testing on the flexural strength of the uncut intact fine ceramic test sample, precuring is also required;

the step of precuring includes:
selecting at least 5 groups of fine ceramic test samples with different flexural strength according to the grades of flexural strength, each group including at least 10 fine test samples with the same flexural strength;
placing the selected fine ceramic test samples in an environment with a temperature of 20° C.±2° C. and a relative humidity of 60%±5% for standing and curing for 48 h to obtain cured fine ceramic test samples.

Further, the step of adjusting the ultrasonic testing instrument, controlling and adjusting the positions of the ultrasonic testing probes of the ultrasonic testing instrument till the ultrasonic testing probes, the fine ceramic test sample and the resiling direction are located on the same plane, performing ultrasonic testing on the test sample, and collecting the ultrasonic testing data of the test sample specifically includes:

connecting an ultrasonic transmitter and an ultrasonic receiver to the ultrasonic testing instrument, and controlling the ultrasonic testing instrument to be in communication connection to the data collection mechanism;
uniformly selecting, in advance, at least 8 testing points that are distributed at an equal interval at the center of each side surface of the test sample in a thickness direction;
adjusting the ultrasonic transmitter and the ultrasonic receiver to the testing points on two opposite side surfaces of the fine ceramic test sample and to be on the same plane as the two opposite side surfaces;
performing ultrasonic testing once on each testing point, and testing data, such as a time difference, a wave velocity and an amplitude at the signal receiving moments of the two ultrasonic testing probes, to obtain an ultrasonic velocity V of each testing point.

Further, the step of adjusting the position of the fine ceramic test sample till the resilience testing rod and the test sample are located on the same plane and fixed, performing resilience testing on the test sample, and collecting the resilience testing data of the test sample specifically includes:

controlling the sample installation component to adjust the fine ceramic test sample to a position located on the same horizontal plane as the resilience testing rod of the resilience testing component;

controlling the resilience testing rod to be perpendicular to the testing points to test resilience values of all the testing points, and collecting resilience testing data of all the side surfaces of the test sample.

Further, the data collection mechanism collects the ultrasonic velocity V of each testing point and a resilience value R in the resilience testing data, takes a mean value of a plurality of ultrasonic velocities V as an ultrasonic velocity effective value and stores the mean value, and takes a mean value of a plurality of resilience values R as a resilience value effective value and stores the mean value. V Further, the data model is $\sigma = A \cdot V^B \cdot R^C$ where:

A is a coefficient factor, a value range of which is $e^{5.0} - e^{35.0}$;

B is a sound wave factor, a value range of which is $-3.5 - 0.0$;

C is a resilience factor, a value range of which is 0.0-2.0;

$\sigma$ is the flexural strength, the unit of which is MPa;

V is the ultrasonic velocity, the unit of which is m/s;

R is the resilience value.

Further, the non-destructive testing method for flexural strength of fine ceramic further includes:

performing testing according to the grades of flexural strength to form a regression analysis sample, and fitting and creating a relation curve of resilience-ultrasonic for testing the flexural strength of the fine ceramic;

using the built data model according to the obtained resilience effective value and the ultrasonic effective value to perform calculation and analysis to obtain the flexural strength $\sigma$;

obtaining an effective numerical value of the flexural strength $\sigma$ of each test sample in each group, and taking an arithmetic mean value as the flexural strength $\sigma'$ of the group of test samples.

Another technical solution adopted by the present disclosure to solve the technical problems is as follows: an apparatus, which includes a memory, a processor, and a non-destructive testing program for flexural strength of fine ceramic that is stored on the memory and is operable on the processor. The non-destructive testing program for flexural strength of fine ceramic, when executed by the processor, realizes the steps of the above-mentioned non-destructive testing method for flexural strength of fine ceramic.

A further technical solution adopted by the present disclosure to solve the technical problems is as follows: a storage medium. The storage medium stores a computer program which can be executed to implement the above-mentioned non-destructive testing method for flexural strength of fine ceramic.

Beneficial effects: The present disclosure provides a non-destructive testing method for flexural strength of fine ceramic, an apparatus, and a storage medium. The non-destructive testing method for flexural strength of fine ceramic includes: adjusting the uncut intact fine ceramic test sample to the ultrasonic testing position, and fixing the test sample; adjusting the ultrasonic testing instrument, controlling and adjusting the positions of the ultrasonic testing probes of the ultrasonic testing instrument till the ultrasonic testing probes, the fine ceramic test sample and the resiling direction are located on the same plane, performing ultrasonic testing on the test sample, and collecting the ultrasonic testing data of the test sample; adjusting the position of the fine ceramic test sample till a resilience testing rod and the test sample are located on the same plane and fixed, performing resilience testing on the test sample, and collecting the resilience testing data of the test sample; and building the data model according to the ultrasonic testing data and the resilience testing data, or substituting the ultrasonic testing data and the resilience testing data into the pre-built data model to obtain the flexural strength characterization data of the test sample. According to the non-destructive testing method for flexural strength of fine ceramic provided by the present disclosure, the fine ceramic test sample does not need to be tailored and cut into small-size test samples and will not be destroyed; the intact fine ceramic is directly subjected to non-destructive testing, so that the material itself cannot be destroyed, the accuracy of the tested data is improved, damage to the test sample is also avoided, and reuse of the test sample is realized.

DETAILED DESCRIPTION OF THE EMBODIMENTS

To make the objectives, technical solutions and advantages of the present disclosure clearer, the present disclosure is further described below in detail with reference to accompanying drawings and embodiments. It should be understood that the specific embodiments described here are merely to explain the present disclosure, and not intended to limit the present disclosure.

At present, the testing of the flexural strength for fine ceramic products mainly refers to the standard GB/T6569-2006 "Fine Ceramics (advanced Ceramics, advanced Technical Ceramics)—Test Method for Flexural Strength of Monolithic Ceramics At Room Temperature", and is carried out by destructive testing measures or methods. A non-destructive testing method has not been widely accepted at home and abroad to characterize the flexural strength. Existing testing methods mainly have the following problems in actual operation:

(1) Most of existing testing methods or devices for flexural strength of fine ceramic are not suitable for test samples of large-size or specially-shaped products (such as a platy product having an upper surface area larger than or equal to 1.62 m², a hollow product, an arc-shaped product, or a product of a specially-shaped structure). A test sample can be tested only after it is machined into an appropriate size or a sample prepared under the same conditions can be tested. For some fine ceramic with ultra-high strength, their strength cannot be accurately characterized even if a destructive method is used for testing due to the restriction of the natural ability of a testing device.

(2) In a traditional destructive test for testing the flexural strength, samples are selected for testing by a sampling method such as random sampling and systematic sampling; their testing data is used as real strength indicators of a batch of materials and has a certain probability or error. For large-size fine ceramic, an original test sample needs to be tailored, cut and machined to prepare samples, which destroys the elastic modulus property of the test sample itself to a certain extent, causing a larger error in an elastic modulus test result of the test sample.

(3) After a destructive test, a sample to be tested cannot be reused, resulting in great waste. For a large-size fine ceramic sheet (such as having an upper surface area larger than or equal to 1.6 m$^2$), greater waste will be caused.

(4) According to the requirements of some use occasions, fine ceramic products need to be made into tubular or hollow structures, so that they cannot be subjected to destructive testing. These products are only substituted by samples that are made under the same process conditions and meet relevant standard specifications for testing to characterize their strength, so that there is a certain boundedness.

The present disclosure provides a non-destructive testing method for flexural strength of fine ceramic, an apparatus, and a storage medium. An ultrasonic-resiling method is used to test the flexural strength of an inorganic non-metal plate, and a non-destructive testing model for ultrasonic and resilience parameters and the flexural strength of a non-metal material is built. Moreover, the following problems are solved:

First, the problems, caused by the fact that the material will no longer be used and become a waste after traditional fine ceramic is subjected to destructive flexural testing, of waste of resources, environmental pollution and economical loss are solved.

Second, during strength testing of the traditional fine ceramic, a standard test sample that meets a specified size requirement needs to be prepared if the product is of an irregular size. The present disclosure solves the problems that the whole testing process is tedious and the testing period is long, and avoids influence caused by a nonstandard machined test sample.

Third, the non-destructive testing method adopted in the present disclosure can enlarge the sample capacity, and even realize 100% sampling inspection, thereby solving the problem that test samples are not representative enough for the overall performance of a product because of a small number of test samples for sampling inspection, and realizing testing for products that have been put into operation.

The method of the present disclosure can directly test the flexural strength of a fine ceramic material without cutting and tailoring the original characteristic of the material, so that the accuracy of a test result is guaranteed, and the fine ceramic material still can be normally used after normal use to avoid waste of resources. The method has a positive facilitation function for quality control in a production process and selection and quality monitoring for materials in a use process, and is of positive significance for pushing the industrial technology to progress.

Figure 1:
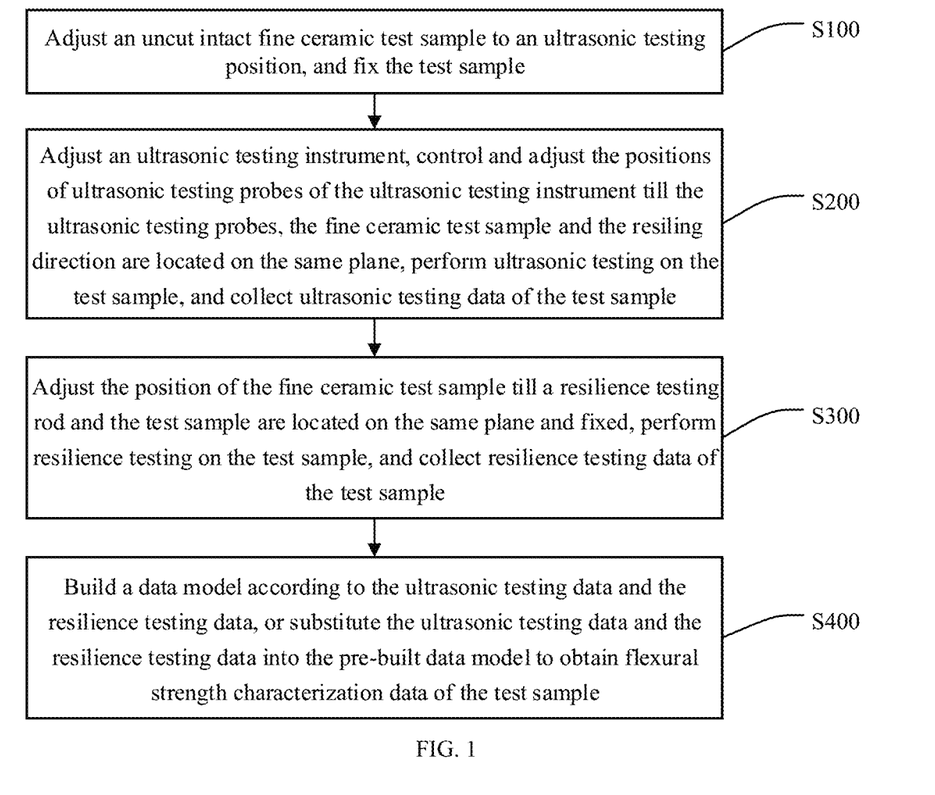
FIG. 1 is a flow diagram of a preferred embodiment of a non-destructive testing method for flexural strength of fine ceramic in the present disclosure.

Referring to FIG. 1, FIG. 1 is a flow diagram of a non-destructive testing method for flexural strength of fine ceramic provided by the present disclosure. The non-destructive testing method for flexural strength of fine ceramic includes:

S100, an uncut intact fine ceramic test sample is adjusted to an ultrasonic testing position, and fixed.

It can be understood that the fine ceramic test sample in the non-destructive testing method for flexural strength of fine ceramic provided by the present disclosure is not subjected to any tailoring or cutting treatment. Regardless of the original shape and the original size of the fine ceramic test sample, the intact test sample is directly subjected to the flexural strength testing. Therefore, the accuracy of the flexural strength testing of the fine ceramic is effectively guaranteed; and the fine ceramic test sample will not be destroyed, so that the waste of resources occurring after the fine ceramic test sample is tested is avoided.

In some preferred embodiments, before the step S100, the method further includes:

S11, an ultrasonic and resilience two-parameter-based non-destructive testing system for flexural strength of fine ceramic is pre-built.

The non-destructive testing system for flexural strength of fine ceramic includes an automatic control and testing mechanism and a data processing mechanism.

Further, the automatic control and testing mechanism includes a sample installation component and a resilience testing component.

Specifically, the present disclosure firstly builds the ultrasonic and resilience two-parameter-based non-destructive testing system for flexural strength of fine ceramic. The system includes the automatic control and testing mechanism and the data processing mechanism. The automatic testing module includes the sample installation component and the testing component. It can be understood that in the non-destructive testing method for flexural strength of fine ceramic provided in the present disclosure, the position of the fine ceramic test sample is adjusted through the sample installation component and fixed; and then, the fine ceramic test sample is tested through the resilience testing component to realize automatic testing of a flexural modulus of the fine ceramic test sample.

In some other preferred embodiments, before the step S100, the method further includes:
  before non-destructive testing is performed on the flexural strength of the uncut intact fine ceramic test sample, precuring is also required.

The step of precuring includes:
  at least 5 groups of fine ceramic test samples with different flexural strength are selected according to the grades of flexural strength, each group including at least 10 fine test samples with the same flexural strength;
  the selected fine ceramic test samples are placed in an environment with a temperature of 20° C.±2° C. and a relative humidity of 60%±5% for standing and curing for 48 h to obtain cured fine ceramic test samples.

It can be understood that in order to ensure that conditions are uniform before the fine ceramic test sample is subjected to the flexural strength testing, the repetitiveness of the flexural strength of the same fine ceramic test sample is improved. Since the fine ceramic test sample is pre-cured, the accuracy of the test result of the flexural strength of the fine ceramic test sample is guaranteed.

Figure 2:
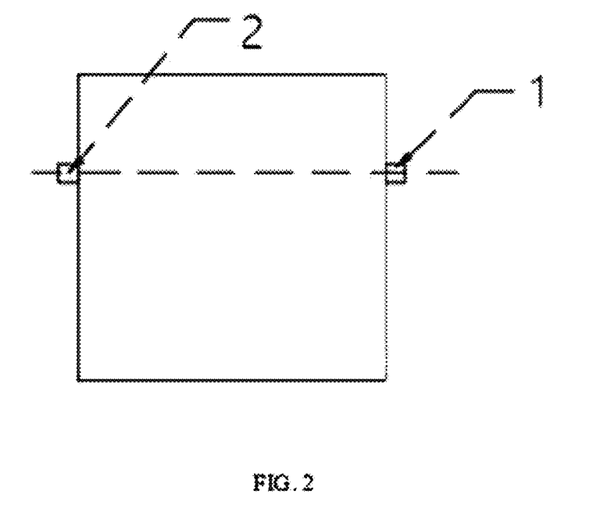
FIG. 2 is a flow diagram of ultrasonic testing in a preferred embodiment of a non-destructive testing method for flexural strength of fine ceramic in the present disclosure.

Step S200, an ultrasonic testing instrument is adjusted; the positions of ultrasonic testing probes of the ultrasonic testing instrument are controlled and adjusted till the ultrasonic testing probes, the fine ceramic test sample and a resiling direction are located on the same plane; ultrasonic testing is performed on the test sample, and ultrasonic testing data of the test sample is collected.

Specifically, the step S100 specifically includes:

Step S110, an ultrasonic transmitter and an ultrasonic receiver are connected to the ultrasonic testing instrument, and the ultrasonic testing instrument is controlled to be in communication connection to the data collection mechanism;

Step S120, at least 8 testing points that are distributed at an equal interval are uniformly selected in advance at the center of each side surface of the test sample in a thickness direction;

Step S130, the ultrasonic transmitter and the ultrasonic receiver are adjusted to the testing points on two opposite side surfaces of the fine ceramic test sample and are on the same plane as the two opposite side surfaces;

Step S140, ultrasonic testing is performed once on each testing point, and data, such as a time difference, a wave velocity and an amplitude at the signal receiving moments of the two ultrasonic testing probes, is tested to obtain an ultrasonic velocity V of each testing point.

It can be understood that after the fine ceramic test sample is fixed at the ultrasonic testing position, the ultrasonic testing instrument is controlled, the ultrasonic transmitter and the ultrasonic receiver are connected to the ultrasonic testing instrument, and the ultrasonic testing instrument is in communication connection to the data collection mechanism, so that the data collection mechanism is ensured to accurately collect the ultrasonic testing data of the fine ceramic test sample; moreover, at least 8 testing points that are distributed at an equal interval are uniformly selected at the center of each side surface of the fine ceramic test sample in the thickness direction to ensure accurate collection of the ultrasonic testing data on each surface; and finally, the ultrasonic transmitter and the ultrasonic receiver are adjusted to be kept on a uniform plane with the fine ceramic test sample, thereby effectively guaranteeing the accuracy of ultrasonic data testing.

Step S300, the position of the fine ceramic test sample is adjusted till a resilience testing rod and the test sample are located on the same plane and fixed; resilience testing is performed on the test sample; and resilience testing data of the test sample is collected.

Specifically, the step S300 specifically includes:

Step S310, the sample installation component is controlled to adjust the fine ceramic test sample to a position located on the same horizontal plane as the resilience testing rod of the resilience testing component;

Step S320, the resilience testing rod is controlled to be perpendicular to the testing points to test resilience values of all the testing points, and resilience testing data of all the side surfaces of the test sample is collected.

It can be understood that after the ultrasonic testing of the test sample is completed, the sample installation component in the automatic control and testing mechanism adjusts the position of the test sample to adjust the fine ceramic test sample to the position located on the same horizontal plane as the resilience testing rod of the resilience testing component. That is, the resilience testing rod is perpendicularly aligned with the equally-spaced testing points arranged on the center lines on the side surfaces of the fine ceramic in the thickness directions; the testing points should be spaced by at least 20 mm or farther, and be uniformly distributed on the side surfaces. After the testing points are set, a resiliometer is automatically adjusted and perpendicularly aligned with the testing points of the test sample to test the resilience values of all the testing points on each side surface of the test sample to obtain resilience value parameters, i.e., the resilience testing data, of this side, further improving the testing accuracy.

In some preferred embodiments, each testing point is subjected to ultrasonic testing and resilience testing only once. The data collection mechanism collects the ultrasonic velocity V of each testing point and a resilience value R in the resilience testing data, takes a mean value of a plurality of ultrasonic velocities V as an ultrasonic velocity effective value and stores the mean value, and takes a mean value of a plurality of resilience values R as a resilience value effective value and stores the mean value.

It can be understood that since the mean value of the ultrasonic velocities is taken as the ultrasonic velocity effective value, and the mean value of the plurality of resilience values R is taken as the resilience value effective value, the accuracy of the flexural strength of the fine ceramic test sample is guaranteed.

In some preferred embodiments, the data model is $\sigma = A \cdot V^B \cdot R^C$ where A is a coefficient factor, a value range of which is $e^{5.0}$–$e^{35.0}$; B is a sound wave factor, a value range of which is −5.0–0.0; C is a resilience factor, a value range of which is 0.0-2.0; σ is the flexural strength, the unit of which is MPa; V is the ultrasonic velocity, the unit of which is m/s; and R is the resilience value.

In some other preferred embodiments, the non-destructive testing method for flexural strength of fine ceramic further includes:

performing testing according to the grades of flexural strength to form a regression analysis sample, and fitting and creating a relation curve of resilience-ultrasonic for testing the flexural strength of the fine ceramic;

the built data model is used according to the obtained resilience effective value and the ultrasonic effective value to perform calculation and analysis to obtain the flexural strength σ;

an effective numerical value of the flexural strength σ of each test sample in each group is obtained, and an arithmetic mean value is taken as the flexural strength σ' of the group of test samples.

Specifically, for different fine ceramic materials, testing is performed according to the grades of flexural strength to form a regression analysis sample, and the relation curve of resilience-ultrasonic for testing the flexural strength of the fine ceramic material is fitted and created. Data processing is then performed: the effective values of the resilience value R and the ultrasonic propagation velocity V of each testing point are obtained in the testing process, and the mean values are respectively taken as the resilience value and the ultrasonic velocity value of the test sample; a regression equation is used for calculation and analysis to obtain the flexural strength value σ; an effective numerical value of the flexural strength value σ of each test sample of each group is obtained, and an arithmetic mean value is taken as a flexural strength representative value σ' of the group of test samples.

It can be known that the present disclosure has the following advantages: Firstly, the flexural strength of a fine ceramic material can be tested without destroying the original texture and shape of the fine ceramic material. Secondly, the present disclosure can obtain a result within short time without destroying the original characteristics of the material for relevant personnel to make a judgment, which is favorable for the continuity of production and improves the production efficiency. The material is better put to good use in the use process, which lowers the use risk and reduces the waste of resources. Thirdly, the present disclosure can perform the testing in the use process of the material, evaluate whether the material is destroyed or has reduced strength in the use process or other conditions, and provide an effective evaluation reference for the safety condition of the material in the use process.

One embodiment is exemplified below. Testing steps are as follows:
- a, one batch of $Al_2O_3$ fine ceramic test samples having a flexural strength ranging from 400 GPa to 1000 GPa and having the same specification of 150 mm×150 mm are selected;
- b, the non-destructive testing system for flexural strength of a fine ceramic material constructed in the above-mentioned embodiment is used to perform testing according to the above-mentioned non-destructive testing method for flexural strength of fine ceramic to obtain effective values of resilience values R and ultrasonic velocities V. Specific testing steps are:
  1) the fine ceramic test samples are put into the sample installation component and then fixed, and are adjusted to an ultrasonic testing position;
  2) an ultrasonic transmitting probe 1 and an ultrasonic receiving probe 2 of an ultrasonic testing instrument are respectively connected to two ends of the ultrasonic testing instrument, and the ultrasonic testing instrument is in communication connection to the data collection mechanism; the ultrasonic transmitting probe 1 and the ultrasonic receiving probe 2 are respectively connected to two opposite side surfaces of the test samples to obtain data, such as a time difference, a wave velocity and an amplitude at the signal receiving moments of the two sensors, and not all the side surfaces of the test samples are subjected to the ultrasonic testing; the ultrasonic testing is completed to obtain data, such as ultrasonic velocities and frequencies;
  3) the positions of the test samples are adjusted to a resilience testing position till a resilience testing rod and testing points are located on the same horizontal plane; the testing points are center points on side edges of the test samples in a thickness direction; two testing points should be spaced by at least 20 mm or farther; after the testing points are set, a resiliometer is automatically adjusted and perpendicular to the testing points of the test samples to test resilience value of the testing points on all the surfaces to obtain resilience value parameters of the test samples;
  4) The flexural strength performance of the tested fine ceramic is tested according to the standard testing method: GB/T6569-2006 "Fine Ceramics (advanced Ceramics, advanced Technical Ceramics)—Test Method for Flexural Strength of Monolithic Ceramics At Room Temperature" to obtain effective values of the flexural strength σ. Testing data corresponding to the resilience values R, the ultrasonic velocities V and the flexural strength σ of each group of test samples is as shown in Table 1.

TABLE 1

Test results of the resilience values, the ultrasonic velocities and the flexural strength of fine ceramic

| | Serial number | | | | | |
|---|---|---|---|---|---|---|
| | 1 | 2 | 3 | 4 | 5 | 6 |
| Resilience value | 24 | 26 | 28 | 32 | 35 | 37 |
| Propagation velocity m/s | 998.65 | 998.69 | 1004.99 | 1007.17 | 1022.84 | 1037.15 |
| Flexural strength MPa | 475.5 | 512.81 | 591.66 | 611.61 | 647.28 | 663.72 |

A fitting relation equation for the resilience value, the ultrasonic velocity and the flexural strength of the test samples is $\sigma = A \cdot V^B \cdot R^C$ where A is a coefficient factor; B is a sound wave factor; C is a resilience factor; σ is the flexural strength, the unit of which is MPa; V is the ultrasonic velocity, the unit of which is m/s; and R is the resilience value.

By means of data processing and analysis, $A=e^{19.015}$, $B=-2.284$, $C=0.9268$. An equation is: $\sigma = e^{19.015} V^{-2.284} \times R^{0.9268}$.

According to the above-mentioned testing steps, other batches of $Al_2O_3$ fine ceramic of a size of 300×300 mm are randomly selected for verification. Inferential values of the flexural strength calculated by using the resilience values and the ultrasonic velocities are compared with actually tested values of the flexural strength to verify the reliability of the testing method and the fitting equation. Comparison of test results is as shown in Table 2:

TABLE 2

Test results of verification test

| | Serial number | | | | |
|---|---|---|---|---|---|
| | 1 | 2 | 3 | 4 | 5 |
| Resilience value | 25 | 28 | 30 | 31 | 36 |
| Ultrasonic velocity m/s | 999.36 | 1005.62 | 1008.33 | 1011.86 | 1032.67 |
| Inferential values of the flexural strength | 504.06. | 551.96 | 584.80 | 598.05 | 655.74 |
| Actually tested values of the flexural strength | 495.62 | 539.71 | 592.62 | 612.37 | 660.82 |

The verification shows that by comparison between the actually tested values and the inferential values of the test samples, a largest error is 2.3%, which indicates that the error is smaller.

Figure 3:
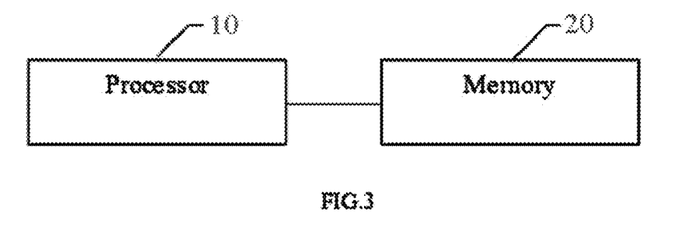
FIG. 3 is a block diagram of a working principle of a preferred embodiment of an apparatus in the present disclosure.

Referring to FIG. 3, the present disclosure further provides an apparatus, which includes a memory 20, a processor 10, and a non-destructive testing program for flexural strength of fine ceramic that is stored on the memory 20 and is operable on the processor 10. The non-destructive testing program for flexural strength of fine ceramic, when executed by the processor, realizes the steps of the above-mentioned non-destructive testing method for flexural strength of fine ceramic, specifically as mentioned above.

The present disclosure further provides a storage medium. The storage medium stores a computer program which can be executed to implement the above-mentioned non-destructive testing method for flexural strength of fine ceramic, specifically as mentioned above.

According to the above, in the non-destructive testing method for flexural strength of fine ceramic, the apparatus and the storage medium, by means of building the relational formulas and curves of the resilience value, the ultrasonic velocity and the flexural strength of the fine ceramic material, the flexural strength of the fine ceramic material is calculated and inferred by using the resilience value and the ultrasonic velocity. Non-destructive testing for the test sample is realized, and higher accuracy and correlation are further achieved; and the sample capacity of the test sample can also be enlarged according to the steps of the present disclosure to obtain relevant formulas.

It should be understood that the application of the present disclosure is not limited to the above-mentioned examples. Those of ordinary skill in the art can make improvements or transformations according to the above illustrations, and all these improvements and transformations shall fall within the protection scope of the claims appended.

What is claimed is:

1. A non-destructive testing method for flexural strength of fine ceramic comprising:
    adjusting an uncut intact fine ceramic test sample to an ultrasonic testing position;
    fixing the uncut intact fine ceramic test sample;
    adjusting an ultrasonic testing instrument;
    controlling and adjusting the positions of ultrasonic testing probes of the ultrasonic testing instrument until the ultrasonic testing probes, the uncut intact fine ceramic test sample are located on the same plane;
    performing ultrasonic testing on the uncut intact fine ceramic test sample;
    collecting ultrasonic testing data of the uncut intact fine ceramic test sample;
    adjusting the position of the uncut intact fine ceramic test sample until a resilience testing rod and the uncut intact fine ceramic test sample are located perpendicular to one another and fixed;
    performing resilience testing on the uncut intact fine ceramic test sample;
    performing testing according to grades of flexural strength to form a regression analysis sample;
    collecting resilience testing data of the uncut intact fine ceramic test sample; and
    obtaining, based upon a data model using the ultrasonic testing data and the resilience testing data, flexural strength characterization data of the uncut intact fine ceramic test sample.

2. The non-destructive testing method for the flexural strength of the fine ceramic according to claim 1, wherein before adjusting the uncut intact fine ceramic test sample to the ultrasonic testing position and fixing the uncut intact fine ceramic test sample, the non-destructive testing method further comprises:
    pre-constructing an ultrasonic and resilience two-parameter-based non-destructive testing system for flexural strength of fine ceramic, wherein the non-destructive testing system for flexural strength of fine ceramic comprises an automatic control and testing mechanism and a data processing mechanism; and the automatic testing mechanism also comprises a sample installation component, an ultrasonic testing component, and a resilience testing component.

3. The non-destructive testing method for the flexural strength of the fine ceramic according to claim 2, wherein before performing non-destructive testing on the flexural strength of the uncut intact fine ceramic test sample, pre-curing is also required and comprises:
    selecting at least five groups of fine ceramic test samples with different flexural strength according to the grades of flexural strength, each group comprising at least ten fine test samples with the same flexural strength; and
    placing the selected at least five groups of fine ceramic test samples in an environment with a temperature of 20° C.±2° C. and a relative humidity of 60%±5% for standing and curing for 48 h to obtain cured fine ceramic test samples.

4. The non-destructive testing method for the flexural strength of the fine ceramic according to claim 3, wherein the step of adjusting the ultrasonic testing instrument, controlling and adjusting the positions of the ultrasonic testing probes of the ultrasonic testing instrument until the ultrasonic testing probes, the uncut intact fine ceramic test sample are located on the same plane, performing ultrasonic testing on the uncut intact fine ceramic test sample, and collecting ultrasonic testing data of the uncut intact fine ceramic test sample further comprise:
    connecting an ultrasonic transmitter and an ultrasonic receiver to the ultrasonic testing instrument;
    controlling the ultrasonic testing instrument to be in communication connection to the data collection mechanism;
    uniformly selecting, in advance, at least eight testing points that are distributed at an equal interval at the center of each side surface of the uncut intact fine ceramic test sample in a thickness direction;
    adjusting the ultrasonic transmitter and the ultrasonic receiver to the at least eight testing points on two opposite side surfaces of the uncut intact fine ceramic test sample and to be on the same plane as the two opposite side surfaces; and
    performing ultrasonic testing once on each testing point, and testing data, such as a time difference, a wave velocity and an amplitude at the signal receiving moments of the two ultrasonic testing probes, to obtain an ultrasonic velocity V of each testing point.

5. The non-destructive testing method for the flexural strength of the fine ceramic according to claim 4, wherein the step of adjusting the position of the uncut intact fine ceramic test sample until the resilience testing rod and the uncut intact fine ceramic test sample are located perpendicular to one another and fixed, performing resilience testing on the uncut intact fine ceramic test sample, and collecting the resilience testing data of the uncut intact fine ceramic test sample further comprise:
    controlling the sample installation component to adjust the uncut intact fine ceramic test sample to a position located on the same horizontal plane as the resilience testing rod of the resilience testing component;
    controlling the resilience testing rod to be perpendicular to the testing points to test resilience values of all the testing points; and
    collecting resilience testing data of all the side surfaces of the uncut intact fine ceramic test sample.

6. The non-destructive testing method for the flexural strength of the fine ceramic according to claim 5, further comprising:
    collecting, with the data collection mechanism, the ultrasonic velocity V of each testing point and a resilience value R in the resilience testing data;
    taking a mean value of a plurality of ultrasonic velocities V as an ultrasonic velocity effective value;
    storing the mean value of the plurality of ultrasonic velocities V;
    taking a mean value of a plurality of resilience values R as a resilience value effective value; and storing the mean value of the plurality of resilience values R.

7. The non-destructive testing method for the flexural strength of the fine ceramic according to claim 5, wherein the data model is $\sigma = A \cdot V^B \cdot R^C$ A is a coefficient factor, a value range of which is $e^{5.0}$–$e^{35.0}$;

B is a sound wave factor, a value range of which is −3.5–0.0;

C is a resilience factor, a value range of which is 0.0-2.0;

$\sigma$ is a flexural strength, a unit of which is MPa;

V is a ultrasonic velocity, a unit of which is m/s, and;

R is a resilience value.

8. The non-destructive testing method for the flexural strength of the fine ceramic according to claim 3, further comprising:

fitting and creating a resilience-ultrasonic relation curve for testing the flexural strength of the fine ceramic;

using the data model according to an obtained resilience effective value and an ultrasonic effective value to perform calculation and analysis to obtain the flexural strength $\sigma$;

obtaining an effective numerical value of a flexural strength $\sigma$; and taking an arithmetic mean value as the flexural strength $\sigma$'.

9. An apparatus, comprising a memory, a processor, and a non-destructive testing program for flexural strength of fine ceramic that is stored on the memory and is operable on the processor, wherein a testing program for flexural strength of fine ceramic, when executed by the processor, realizes the steps of the non-destructive testing method for flexural strength of fine ceramic according to claim 1.

10. A non-transitory storage medium configured to store a computer program which may be executed to implement the non-destructive testing method for flexural strength of fine ceramic according to claim 1.

* * * * *